United States Patent
Wortz

(10) Patent No.: US 11,033,381 B2
(45) Date of Patent: Jun. 15, 2021

(54) PROSTHETIC CAPSULAR DEVICES, SYSTEMS, AND METHODS

(71) Applicant: Omega Ophthalmics LLC, Versailles, KY (US)

(72) Inventor: Gary N. Wortz, Nicholasville, KY (US)

(73) Assignee: Omega Ophthalmics LLC, Versailles, KY (US)

(*) Notice: Subject to any disclaimer, the term of this patent is extended or adjusted under 35 U.S.C. 154(b) by 0 days.

(21) Appl. No.: 17/157,669

(22) Filed: Jan. 25, 2021

(65) Prior Publication Data

US 2021/0145568 A1 May 20, 2021

Related U.S. Application Data

(63) Continuation of application No. 17/037,271, filed on Sep. 29, 2020, which is a continuation of application No. 16/135,806, filed on Sep. 19, 2018, now Pat. No. 10,820,985, which is a continuation of application No. 14/551,544, filed on Nov. 24, 2014, now Pat. No. 10,136,989, which is a continuation of application
(Continued)

(51) Int. Cl.
*A61F 2/14* (2006.01)
*A61F 2/16* (2006.01)

(52) U.S. Cl.
CPC .............. *A61F 2/14* (2013.01); *A61F 2/1648* (2013.01); *A61F 2/1694* (2013.01); *A61F 2/16* (2013.01); *A61F 2/1662* (2013.01)

(58) Field of Classification Search
CPC .. A61F 2/1694; A61F 2/16; A61F 2/14; A61F 2/1648; A61F 2/1662; A61F 2002/16901
See application file for complete search history.

(56) References Cited

U.S. PATENT DOCUMENTS

| 4,073,014 A | 2/1978 | Poler |
| 4,373,218 A | 2/1983 | Schachar |
| 4,402,579 A | 10/1983 | Poler |

(Continued)

FOREIGN PATENT DOCUMENTS

| CA | 2 864 882 | 6/2015 |
| EP | 0 337 390 | 2/1993 |

(Continued)

OTHER PUBLICATIONS

Allergan, "Positive Phase I/II Interim Data of Bimatoprost Sustained-Release Implant for IOP Therapy in Glaucoma", Nov. 16, 2015, http://www.allergan.com/NEWS/News/Thomson-Reuters/Positive-Phase-I-II-Interim-Data-of-Bimatoprost-Su in 4 pages.

(Continued)

*Primary Examiner* — Dinah Baria
(74) *Attorney, Agent, or Firm* — Knobbe Martens Olson & Bear LLP

(57) ABSTRACT

The present invention relates to a prosthetic capsular bag and method for inserting the same. The prosthetic capsular bag helps to maintain the volume of the natural capsular bag, thereby stabilizing the effective lens position of an IOL so that refractive outcomes may be improved with cataract surgery. The prosthetic capsular bag further provides an integrated refractive surface, providing a means for experimentally determining an effective lens position prior to inserting an IOL.

30 Claims, 7 Drawing Sheets

Related U.S. Application Data

No. 13/402,398, filed on Feb. 22, 2012, now Pat. No. 8,900,300.

(56) References Cited

U.S. PATENT DOCUMENTS

| | | | |
|---|---|---|---|
| 4,423,856 A | 1/1984 | Takahashi et al. |
| 4,435,856 A | 3/1984 | L'Esperance |
| 4,575,373 A | 3/1986 | Johnson |
| 4,585,456 A | 4/1986 | Blackmore |
| 4,629,461 A | 12/1986 | Clayman et al. |
| 4,685,921 A | 8/1987 | Peyman |
| 4,704,124 A | 11/1987 | Shearing |
| 4,731,078 A | 3/1988 | Stoy et al. |
| 4,816,031 A | 3/1989 | Pfoff |
| 4,833,890 A | 5/1989 | Kelman |
| 4,842,601 A | 6/1989 | Smith |
| 4,888,012 A | 12/1989 | Horn et al. |
| 4,888,016 A | 12/1989 | Langerman |
| 4,892,543 A | 1/1990 | Turley |
| 4,932,966 A | 6/1990 | Christie et al. |
| 5,147,395 A | 9/1992 | Willis |
| 5,171,266 A | 12/1992 | Wiley et al. |
| 5,180,390 A | 1/1993 | Drews |
| 5,203,788 A | 4/1993 | Wiley |
| 5,222,981 A | 6/1993 | Werblin |
| 5,275,623 A | 1/1994 | Sarfarazi |
| 5,326,347 A | 7/1994 | Cumming |
| 5,358,520 A | 10/1994 | Patel |
| 5,522,891 A | 6/1996 | Klaas |
| 5,562,731 A | 10/1996 | Cumming |
| 5,628,795 A | 5/1997 | Langerman |
| 5,628,798 A | 5/1997 | Eggleston et al. |
| 5,653,751 A | 8/1997 | Samiy et al. |
| 5,674,282 A | 10/1997 | Cumming |
| 5,676,669 A | 10/1997 | Colvard |
| 5,697,973 A | 12/1997 | Peyman et al. |
| 5,702,402 A | 12/1997 | Brady |
| 5,800,533 A | 9/1998 | Eggleston et al. |
| 5,964,802 A | 10/1999 | Anello et al. |
| 5,968,094 A | 10/1999 | Werblin et al. |
| 5,984,962 A | 11/1999 | Anello et al. |
| 6,015,435 A | 1/2000 | Valunin |
| 6,027,531 A | 2/2000 | Tassignon |
| 6,113,633 A | 9/2000 | Portney |
| 6,117,171 A | 9/2000 | Skottun |
| 6,136,026 A | 10/2000 | Israel |
| 6,143,244 A | 11/2000 | Xia et al. |
| 6,217,612 B1 | 4/2001 | Woods |
| 6,235,055 B1 | 5/2001 | Chu |
| 6,280,471 B1 | 8/2001 | Peyman et al. |
| 6,299,641 B1 | 10/2001 | Woods |
| 6,322,589 B1 | 11/2001 | Cumming |
| 6,413,276 B1 | 7/2002 | Werblin |
| 6,428,574 B1 | 8/2002 | Valunin |
| 6,443,985 B1 | 9/2002 | Woods |
| 6,450,642 B1 | 9/2002 | Jethmalani et al. |
| 6,454,801 B1 | 9/2002 | Portney |
| 6,464,725 B2 | 10/2002 | Skottun |
| 6,488,708 B2 | 12/2002 | Sarfarazi |
| 6,503,276 B2 | 1/2003 | Lang et al. |
| 6,506,212 B2 | 1/2003 | Zhou et al. |
| 6,524,340 B2 | 2/2003 | Israel |
| 6,533,813 B1 | 3/2003 | Lin et al. |
| 6,537,281 B1 | 3/2003 | Portnoy |
| 6,537,317 B1 | 3/2003 | Steinert |
| 6,576,012 B2 | 6/2003 | Lang |
| 6,596,026 B1 | 7/2003 | Gross |
| 6,645,246 B1 | 11/2003 | Weinschenk |
| 6,695,881 B2 | 2/2004 | Peng et al. |
| 6,721,043 B2 | 4/2004 | Platt et al. |
| 6,749,634 B2 | 6/2004 | Hanna |
| 6,761,737 B2 | 7/2004 | Zadno-Azizi et al. |
| 6,764,511 B2 | 7/2004 | Zadno-Azizi et al. |
| 6,786,934 B2 | 9/2004 | Zadno-Azizi et al. |
| 6,797,004 B1 | 9/2004 | Brady et al. |
| 6,813,097 B2 | 11/2004 | Jethmalani et al. |
| 6,818,158 B2 | 11/2004 | Pham et al. |
| 6,824,266 B2 | 11/2004 | Jethmalani et al. |
| 6,827,738 B2 | 12/2004 | Willis et al. |
| 6,846,326 B2 | 1/2005 | Zadno-Azizi et al. |
| 6,851,804 B2 | 2/2005 | Jethmalani et al. |
| 6,858,040 B2 | 2/2005 | Nguyen et al. |
| 6,881,225 B2 | 4/2005 | Okada |
| 6,884,261 B2 | 4/2005 | Zadno-Azizi et al. |
| 6,884,263 B2 | 4/2005 | Valyunin et al. |
| 6,899,732 B2 | 5/2005 | Zadno-Azizi et al. |
| 6,905,641 B2 | 6/2005 | Platt et al. |
| 6,917,416 B2 | 7/2005 | Platt et al. |
| 6,921,416 B2 | 7/2005 | Khoury |
| 6,926,736 B2 | 8/2005 | Peng et al. |
| 6,960,230 B2 | 11/2005 | Haefliger |
| 6,960,231 B2 | 11/2005 | Tran |
| 6,972,033 B2 | 12/2005 | McNicholas |
| 6,986,900 B2 | 1/2006 | Yaacobi |
| 7,001,374 B2 | 2/2006 | Peyman |
| 7,001,427 B2 | 2/2006 | Aharoni et al. |
| 7,025,783 B2 | 4/2006 | Brady et al. |
| 7,029,497 B2 | 4/2006 | Zhang et al. |
| 7,041,134 B2 | 5/2006 | Nguyen et al. |
| 7,074,840 B2 | 7/2006 | Chang et al. |
| 7,087,080 B2 | 8/2006 | Zadno-Azizi et al. |
| 7,105,110 B2 | 9/2006 | Platt et al. |
| 7,118,596 B2 | 10/2006 | Zadno-Azizi et al. |
| 7,119,894 B2 | 10/2006 | Platt et al. |
| 7,122,053 B2 | 10/2006 | Esch |
| 7,125,422 B2 | 10/2006 | Woods |
| 7,134,755 B2 | 11/2006 | Jethmalani et al. |
| 7,144,423 B2 | 12/2006 | McDonald |
| 7,150,760 B2 | 12/2006 | Zhang |
| 7,198,640 B2 | 4/2007 | Nguyen |
| 7,210,783 B2 | 5/2007 | Jethmalani et al. |
| 7,223,288 B2 | 5/2007 | Zhang et al. |
| 7,226,478 B2 | 6/2007 | Ting et al. |
| 7,237,893 B2 | 7/2007 | Chang et al. |
| 7,241,009 B2 | 7/2007 | Kornfield et al. |
| 7,281,795 B2 | 10/2007 | Sandstedt et al. |
| 7,300,464 B2 | 11/2007 | Tran |
| 7,414,714 B2 | 8/2008 | Platt et al. |
| 7,452,362 B2 | 11/2008 | Zadno-Azizi et al. |
| 7,452,378 B2 | 11/2008 | Zadno-Azizi et al. |
| 7,462,193 B2 | 12/2008 | Nagamoto |
| 7,560,499 B2 | 7/2009 | Jethmalani et al. |
| 7,658,364 B2 | 2/2010 | Robinson et al. |
| 7,662,179 B2 | 2/2010 | Sarfarazi |
| 7,713,299 B2 | 5/2010 | Brady et al. |
| 7,744,603 B2 | 6/2010 | Zadno-Azizi et al. |
| 7,744,646 B2 | 6/2010 | Zadno-Azizi et al. |
| 7,771,471 B2 | 8/2010 | Dell |
| 7,780,729 B2 | 8/2010 | Nguyen et al. |
| 7,798,644 B2 | 9/2010 | Jethmalani et al. |
| 7,806,929 B2 | 10/2010 | Brown |
| 7,811,320 B2 | 10/2010 | Werblin et al. |
| 7,837,326 B2 | 11/2010 | Jethmalani et al. |
| 7,871,437 B2 | 1/2011 | Hermans et al. |
| 7,988,285 B2 | 8/2011 | Sandstedt et al. |
| 7,988,291 B2 | 8/2011 | Ianchulev |
| 8,025,823 B2 | 9/2011 | Pham et al. |
| 8,034,107 B2 | 10/2011 | Stenger |
| 8,048,155 B2 | 11/2011 | Shadduck |
| 8,052,752 B2 | 11/2011 | Woods et al. |
| 8,062,361 B2 | 11/2011 | Nguyen et al. |
| 8,088,161 B2 | 1/2012 | Aharoni et al. |
| 8,100,965 B2 | 1/2012 | Cumming |
| 8,128,693 B2 | 3/2012 | Tran et al. |
| 8,162,927 B2 | 4/2012 | Peyman et al. |
| 8,187,325 B2 | 5/2012 | Zadno-Azizi et al. |
| 8,197,539 B2 | 6/2012 | Nasiatka et al. |
| 8,246,679 B2 | 8/2012 | Nguyen et al. |
| 8,273,123 B2 | 9/2012 | Nun |
| 8,343,216 B2 | 1/2013 | Brady et al. |
| 8,361,353 B2 | 1/2013 | Brait et al. |
| 8,398,709 B2 | 3/2013 | Nun et al. |
| 8,486,142 B2 | 7/2013 | Bumbalough et al. |
| 8,505,822 B2 | 8/2013 | Wang et al. |

(56) References Cited

U.S. PATENT DOCUMENTS

| | | |
|---|---|---|
| 8,506,074 B2 | 8/2013 | Gerbaud |
| 8,545,556 B2 | 10/2013 | Woods et al. |
| 8,556,967 B2 | 10/2013 | Sarfarazi et al. |
| 8,574,295 B2 | 11/2013 | Roholt |
| 8,579,971 B2 | 11/2013 | Webb |
| 8,585,556 B2 | 11/2013 | Woods et al. |
| 8,585,758 B2 | 11/2013 | Woods |
| 8,608,799 B2 | 12/2013 | Blake et al. |
| 8,663,235 B2 | 3/2014 | Tassignon |
| 8,728,158 B2 | 5/2014 | Whitsett |
| 8,778,022 B2 | 7/2014 | Blum et al. |
| 8,821,166 B2 | 9/2014 | Akura et al. |
| 8,834,565 B2 | 9/2014 | Nun |
| 8,900,300 B1 | 12/2014 | Wortz |
| 8,915,588 B2 | 12/2014 | Blum et al. |
| 8,931,896 B2 | 1/2015 | Blum et al. |
| 9,005,282 B2 | 4/2015 | Chang et al. |
| 9,005,283 B2 | 4/2015 | Nguyen et al. |
| 9,039,760 B2 | 5/2015 | Brady et al. |
| 9,072,600 B2 | 7/2015 | Tran |
| 9,078,744 B2 | 7/2015 | Van Noy |
| 9,095,424 B2 | 8/2015 | Kahook et al. |
| 9,119,710 B2 | 9/2015 | Grubbs et al. |
| 9,124,796 B2 | 9/2015 | Blum et al. |
| 9,125,736 B2 | 9/2015 | Kahook et al. |
| 9,149,356 B2 | 10/2015 | Sarfarazi |
| 9,173,527 B2 | 11/2015 | Ulrich et al. |
| 9,186,243 B2 | 11/2015 | Van Noy |
| 9,198,752 B2 | 12/2015 | Woods |
| 9,289,287 B2 | 3/2016 | Kahook et al. |
| 9,339,375 B2 | 5/2016 | Lee et al. |
| 9,358,103 B1 | 6/2016 | Wortz et al. |
| 9,364,316 B1 | 6/2016 | Kahook et al. |
| 9,387,069 B2 | 7/2016 | Kahook et al. |
| 9,414,907 B2 | 8/2016 | Wortz et al. |
| 9,421,088 B1 | 8/2016 | Kahook et al. |
| 9,439,754 B2 | 9/2016 | Wortz |
| 9,504,558 B2 | 11/2016 | Wortz et al. |
| 9,517,127 B2 | 12/2016 | Wortz et al. |
| 9,522,059 B2 | 12/2016 | Wortz et al. |
| 9,522,060 B2 | 12/2016 | Wortz et al. |
| 9,554,890 B2 | 1/2017 | Wortz et al. |
| 9,597,176 B2 | 3/2017 | Wortz et al. |
| 9,629,712 B2 | 4/2017 | Stenger |
| 9,642,699 B2 | 5/2017 | Wortz et al. |
| 9,681,946 B2 | 6/2017 | Kahook et al. |
| 9,763,771 B1 | 9/2017 | Wortz et al. |
| 9,925,037 B2 | 3/2018 | Wortz et al. |
| 9,993,336 B2 | 6/2018 | Wortz et al. |
| 10,004,594 B2 | 6/2018 | Wortz et al. |
| 10,111,746 B2 | 10/2018 | Wortz et al. |
| 10,136,989 B2 | 11/2018 | Wortz et al. |
| 10,271,945 B2 | 4/2019 | Wortz et al. |
| 10,492,903 B1 | 12/2019 | Wortz et al. |
| 10,603,162 B2 | 3/2020 | Wortz et al. |
| 10,743,983 B2 | 8/2020 | Wortz et al. |
| 10,813,745 B2 | 10/2020 | Wortz |
| 10,820,985 B2 | 11/2020 | Wortz |
| 10,842,615 B2 | 11/2020 | Wortz et al. |
| 2001/0047204 A1 | 11/2001 | Zhou et al. |
| 2001/0051825 A1 | 12/2001 | Peterson |
| 2002/0128710 A1 | 9/2002 | Eggleston |
| 2002/0143395 A1 | 10/2002 | Skottun |
| 2002/0173846 A1 | 11/2002 | Blake et al. |
| 2003/0004569 A1 | 1/2003 | Haefliger |
| 2003/0050695 A1 | 3/2003 | Lin et al. |
| 2003/0090624 A1 | 5/2003 | Jethmalani et al. |
| 2003/0149479 A1 | 8/2003 | Snyder et al. |
| 2003/0149480 A1 | 8/2003 | Shadduck |
| 2003/0151831 A1 | 8/2003 | Sandstedt et al. |
| 2003/0176521 A1 | 9/2003 | Jethmalani et al. |
| 2003/0187505 A1 | 10/2003 | Liao |
| 2004/0064182 A1 | 4/2004 | Kelman |
| 2004/0082993 A1 | 4/2004 | Woods |
| 2004/0082995 A1 | 4/2004 | Woods |
| 2004/0106993 A1 | 6/2004 | Portney |
| 2004/0117011 A1 | 6/2004 | Aharoni et al. |
| 2004/0148022 A1 | 7/2004 | Eggleston |
| 2004/0158322 A1 | 8/2004 | Shen et al. |
| 2004/0167622 A1 | 8/2004 | Sunlap et al. |
| 2004/0208910 A1 | 10/2004 | Ashton et al. |
| 2004/0254438 A1 | 12/2004 | Chuck et al. |
| 2005/0021138 A1 | 1/2005 | Woods |
| 2005/0085907 A1 | 4/2005 | Hanna |
| 2005/0099597 A1 | 5/2005 | Sandstedt et al. |
| 2005/0107875 A1 | 5/2005 | Cumming |
| 2005/0113911 A1 | 5/2005 | Peyman |
| 2005/0113913 A1 | 5/2005 | Duvert et al. |
| 2005/0137703 A1 | 6/2005 | Chen |
| 2005/0154457 A1 | 7/2005 | Aharoni et al. |
| 2005/0187623 A1 | 8/2005 | Tassignon |
| 2005/0222577 A1 | 10/2005 | Vaquero |
| 2005/0234285 A1 | 10/2005 | Khoury |
| 2005/0246018 A1 | 11/2005 | Grubbs et al. |
| 2006/0027939 A1 | 2/2006 | Brait et al. |
| 2006/0047339 A1 | 3/2006 | Brown |
| 2006/0064161 A1 | 3/2006 | Blake |
| 2006/0095128 A1 | 5/2006 | Blum et al. |
| 2006/0212116 A1 | 9/2006 | Woods |
| 2006/0253196 A1 | 11/2006 | Woods |
| 2006/0259139 A1 | 11/2006 | Zadno-Azizi et al. |
| 2006/0261502 A1 | 11/2006 | Platt et al. |
| 2007/0027538 A1 | 2/2007 | Aharoni et al. |
| 2007/0027541 A1 | 2/2007 | Aharoni et al. |
| 2007/0032868 A1 | 2/2007 | Woods |
| 2007/0083261 A1 | 4/2007 | Colvard |
| 2007/0093892 A1 | 4/2007 | MacKool |
| 2007/0100444 A1 | 5/2007 | Brady et al. |
| 2007/0118216 A1 | 5/2007 | Pynson |
| 2007/0123767 A1 | 5/2007 | Montegrande et al. |
| 2007/0123981 A1 | 5/2007 | Tassignon |
| 2007/0162118 A1 | 7/2007 | Rozakis et al. |
| 2007/0213816 A1 | 9/2007 | Sarfarazi |
| 2007/0244560 A1 | 10/2007 | Ossipov et al. |
| 2007/0260308 A1 | 11/2007 | Tran |
| 2008/0086206 A1 | 4/2008 | Nasiatka et al. |
| 2008/0097599 A1 | 4/2008 | Rozakis et al. |
| 2008/0221676 A1 | 9/2008 | Coleman et al. |
| 2008/0300680 A1 | 12/2008 | Joshua |
| 2009/0005864 A1 | 1/2009 | Eggleston |
| 2009/0182423 A1 | 7/2009 | Zheng |
| 2010/0022945 A1 | 1/2010 | Rodstrom |
| 2010/0030225 A1 | 2/2010 | Ianchulev |
| 2010/0204788 A1 | 8/2010 | Van Noy |
| 2010/0211171 A1 | 8/2010 | Sarfarazi |
| 2010/0228344 A1 | 9/2010 | Shadduck |
| 2010/0280609 A1 | 11/2010 | Simonov et al. |
| 2011/0015541 A1 | 1/2011 | Padrick et al. |
| 2011/0040378 A1 | 2/2011 | Werblin |
| 2011/0153014 A1 | 6/2011 | Zhang et al. |
| 2011/0181834 A1 | 7/2011 | Gerbaud |
| 2011/0224788 A1 | 9/2011 | Webb |
| 2011/0288638 A1 | 11/2011 | Smiley et al. |
| 2011/0295367 A1 | 12/2011 | Cuevas |
| 2011/0313521 A1 | 12/2011 | Angelopoulos |
| 2012/0078363 A1 | 3/2012 | Lu et al. |
| 2012/0078364 A1 | 3/2012 | Stenger |
| 2012/0179249 A1 | 7/2012 | Coleman |
| 2012/0226351 A1 | 9/2012 | Peyman |
| 2012/0238857 A1 | 9/2012 | Wong et al. |
| 2012/0253458 A1 | 10/2012 | Geraghty et al. |
| 2013/0072591 A1 | 3/2013 | Sandstedt et al. |
| 2013/0116781 A1 | 5/2013 | Nun |
| 2013/0184815 A1 | 7/2013 | Roholt |
| 2013/0190868 A1 | 7/2013 | Kahook et al. |
| 2013/0197637 A1 | 8/2013 | Brait et al. |
| 2013/0245754 A1 | 9/2013 | Blum et al. |
| 2013/0289153 A1 | 10/2013 | Sandstedt et al. |
| 2013/0304206 A1 | 11/2013 | Pallikaris et al. |
| 2013/0310931 A1 | 11/2013 | Kahook et al. |
| 2013/0317458 A1 | 11/2013 | Kopczynski et al. |
| 2014/0052246 A1 | 2/2014 | Kahook et al. |
| 2014/0067059 A1 | 3/2014 | Webb |
| 2014/0172089 A1 | 6/2014 | Lee et al. |

(56) References Cited

U.S. PATENT DOCUMENTS

| | | |
|---|---|---|
| 2014/0228949 A1 | 8/2014 | Argento et al. |
| 2014/0343379 A1 | 11/2014 | Pugh |
| 2014/0371852 A1 | 12/2014 | Aharoni et al. |
| 2014/0379079 A1 | 12/2014 | Ben Nun |
| 2015/0061990 A1 | 3/2015 | Toner et al. |
| 2015/0088253 A1 | 3/2015 | Doll et al. |
| 2015/0100046 A1 | 4/2015 | Ambati et al. |
| 2015/0157452 A1 | 6/2015 | Maliarov et al. |
| 2015/0182330 A1 | 7/2015 | Grant |
| 2015/0230981 A1 | 8/2015 | Kahook et al. |
| 2015/0238309 A1 | 8/2015 | Jansen et al. |
| 2015/0272727 A1 | 10/2015 | Humayun et al. |
| 2015/0289970 A1 | 10/2015 | Akura |
| 2015/0335420 A1 | 11/2015 | Blum et al. |
| 2015/0366660 A1 | 12/2015 | Martinez et al. |
| 2016/0000558 A1 | 1/2016 | Honigsbaum |
| 2016/0008126 A1 | 1/2016 | Salahieh et al. |
| 2016/0030161 A1 | 2/2016 | Brady et al. |
| 2016/0030163 A1 | 2/2016 | Akahoshi |
| 2016/0058552 A1 | 3/2016 | Argal et al. |
| 2016/0058553 A1 | 3/2016 | Salahieh et al. |
| 2016/0074154 A1 | 3/2016 | Woods |
| 2016/0113760 A1 | 4/2016 | Conrad |
| 2016/0113761 A1 | 4/2016 | Nishi et al. |
| 2016/0278912 A1 | 9/2016 | Kahook et al. |
| 2016/0310263 A1 | 10/2016 | Akura |
| 2016/0317287 A1 | 11/2016 | Silverstrini et al. |
| 2016/0324629 A1 | 11/2016 | Sandstedt et al. |
| 2016/0331519 A1 | 11/2016 | Kahook et al. |
| 2016/0339657 A1 | 11/2016 | Grubbs et al. |
| 2017/0000602 A1 | 1/2017 | Sohn et al. |
| 2017/0020658 A1 | 1/2017 | Grubbs et al. |
| 2017/0042667 A1 | 2/2017 | Collins et al. |
| 2017/0049560 A1 | 2/2017 | Cherne |
| 2017/0119521 A1 | 5/2017 | Kahook et al. |
| 2017/0172732 A1 | 6/2017 | Lu et al. |
| 2017/0319332 A1 | 11/2017 | Kahook et al. |
| 2017/0348094 A1 | 12/2017 | Sohn |
| 2019/0076239 A1 | 3/2019 | Wortz et al. |
| 2020/0261216 A1 | 8/2020 | Wortz |

FOREIGN PATENT DOCUMENTS

| | | |
|---|---|---|
| EP | 0 294 039 | 7/1993 |
| EP | 0 528 325 | 12/1996 |
| EP | 0 732 090 | 6/2002 |
| EP | 0 916 320 | 1/2005 |
| EP | 1 653 886 | 5/2006 |
| EP | 1 499 264 | 8/2006 |
| EP | 1 100 411 | 11/2006 |
| EP | 1 694 253 | 8/2007 |
| EP | 1 852 090 | 11/2007 |
| EP | 1 562 521 | 12/2009 |
| EP | 1 475 055 | 4/2010 |
| EP | 1 933 768 | 10/2010 |
| EP | 2 315 559 | 5/2011 |
| EP | 1 438 930 | 9/2011 |
| EP | 2 412 337 | 2/2012 |
| EP | 1 296 616 | 5/2012 |
| EP | 1 906 881 | 8/2012 |
| EP | 2 512 374 | 10/2012 |
| EP | 2 851 038 | 3/2015 |
| EP | 2 620 130 | 7/2016 |
| EP | 2 816 972 | 3/2017 |
| EP | 3 181 095 | 6/2017 |
| EP | 3 157 466 | 12/2017 |
| FR | 2 799 637 | 4/2001 |
| FR | 2 804 860 | 8/2001 |
| FR | 2 966 340 | 4/2012 |
| JP | S63-89154 | 4/1988 |
| JP | 02-011134 | 1/1990 |
| JP | H08-317943 | 12/1996 |
| JP | H09-173363 | 7/1997 |
| JP | 2004-523316 | 6/2005 |
| JP | 2005-143886 | 6/2005 |
| JP | 2007-029727 | 2/2007 |
| JP | 2013-544116 | 12/2013 |
| JP | 5785678 | 9/2015 |
| JP | 2017-519221 | 7/2017 |
| WO | WO 98/017205 | 4/1998 |
| WO | WO 99/024541 | 5/1999 |
| WO | WO 99/062433 | 12/1999 |
| WO | WO 01/64136 | 9/2001 |
| WO | WO 02/026121 | 4/2002 |
| WO | WO 02/071983 | 9/2002 |
| WO | WO 03/058296 | 7/2003 |
| WO | WO 05/016191 | 2/2005 |
| WO | WO 05/094727 | 10/2005 |
| WO | WO 05/107649 | 11/2005 |
| WO | WO 06/002201 | 1/2006 |
| WO | WO 06/050171 | 5/2006 |
| WO | WO 06/124016 | 11/2006 |
| WO | WO 06/135572 | 12/2006 |
| WO | WO 07/030799 | 3/2007 |
| WO | WO 06/015315 | 4/2007 |
| WO | WO 07/121296 | 10/2007 |
| WO | WO 10/002215 | 4/2010 |
| WO | WO 11/163080 | 12/2011 |
| WO | WO 12/067994 | 5/2012 |
| WO | WO 12/161749 | 11/2012 |
| WO | WO 13/039707 | 3/2013 |
| WO | WO 13/112589 | 8/2013 |
| WO | WO 13/126380 | 8/2013 |
| WO | WO 13/158942 | 10/2013 |
| WO | WO 14/167425 | 10/2014 |
| WO | WO 14/197170 | 12/2014 |
| WO | WO 14/201956 | 12/2014 |
| WO | WO 15/044235 | 4/2015 |
| WO | WO 15/066532 | 5/2015 |
| WO | WO 15/126604 | 8/2015 |
| WO | WO 15/195825 | 12/2015 |
| WO | WO 15/198236 | 12/2015 |
| WO | WO 15/200056 | 12/2015 |
| WO | WO 16/122805 | 8/2016 |
| WO | WO 16/187497 | 11/2016 |
| WO | WO 17/030582 | 2/2017 |
| WO | WO 17/079449 | 5/2017 |
| WO | WO 17/192855 | 11/2017 |

OTHER PUBLICATIONS

Becker et al., "Accuracy of Lens Power Calculation and Centration of an Aspheric Intraocular Lens", Der Ophthalmologe: Zeitschrift der Deutschen Ophthalmologischen Gesellschaft, Oct. 2006, 103(10):873-876. [English Abstract].

Guttman-Krader Cheryl , "Small-aperture optic IOL broadens range of vision", Article in Ophthalmology Times on Dec. 1, 2014 in 6 pages.

Kleiman et al., "Post-operative Results with Implantation of the Acrysof SA-60 Intraocular lens into the Ciliary Sulcus", Invest Ophthalmol. Vis Sci. May 2002, 43:E-Abstract 380 in 2 pages.

Kleinmann Guy, "Open-Capsule Device for PCO Prevention", Power Point Presentation for Hanita Lenses, Oct. 17, 2013 in 20 pages.

Koeppl et al., "Change in IOL position and capsular bag size with an angulated intraocular lens early after cataract surgery", J Cataract Refractive Surg. Feb. 2005, 31(2):348-353.

Lim et al., "Surgical management of late dislocated lens capsular bag with intraocular lens and endocapsular tension ring", J Cataract Refractive Surg., Mar. 2006, 32(3):533-535.

Review of Optometry, "Tracking IOP With an IOL", Sep. 15, 2014 in 1 page.

Wirtitsch et al., "Effect of haptic design on change in axial lens posiiton after cataract surgery", J Catar Refractive Surg., Jan. 2004, (30)1:45-51.

International Search report and Written Opinoin dated May 31, 2013 for Application No. PCT/US2013/026820.

International Preliminary Report on Patentability, dated Aug. 26, 2014, in PCT App. No. PCT/US2013/026820.

Office Action issued in European Application No. 13710641.5, dated Oct. 1, 2015, in 5 pages.

(56) References Cited

OTHER PUBLICATIONS

Office Action issued in Japanese Patent Application No. 2014-558790, dated Feb. 3, 2015, in 9 pages.
Notice of Allowance issued in Japanese Patent Application No. 2014-558790, dated Jun. 25, 2015, in 3 pages.
Office Action issued in Japanese Patent Application No. 2015-146248, dated Nov. 28, 2016, in 13 pages.
International Search Report and Written Opinion issued in PCT App. No. PCT/US2015/036263, dated Oct. 7, 2015.
International Preliminary Report on Patentability, dated Dec. 20, 2016, in PCT App. No. PCT/US2015/036263.
International Search Report and Written Opinion issued in PCT Application No. PCT/US2015/065887, dated Apr. 6, 2016.

PROSTHETIC CAPSULAR DEVICES, SYSTEMS, AND METHODS

CROSS-REFERENCE TO RELATED APPLICATIONS

This application is a continuation of U.S. patent application Ser. No. 17/037,271, filed Sep. 29, 2020, which is a continuation of U.S. patent application Ser. No. 16/135,806, filed Sep. 19, 2018, and issued as U.S. Pat. No. 10,820,985 on Nov. 3, 2020, which is a continuation of U.S. patent application Ser. No. 14/551,544, filed Nov. 24, 2014, and issued as U.S. Pat. No. 10,136,989 on Nov. 27, 2018, which is a continuation of U.S. patent application Ser. No. 13/402,398, filed Feb. 22, 2012 and issued as U.S. Pat. No. 8,900,300 on Dec. 2, 2014, each of which is incorporated herein by reference in its entirety under 37 C.F.R. § 1.57. Any and all applications for which a foreign or domestic priority claim is identified in the Application Data Sheet as filed with the present application are hereby incorporated by references in their entirety under 37 C.F.R. § 1.57.

BACKGROUND

(a) Technical Field

The present invention relates to a prosthetic capsular bag and method for inserting the same.

(b) Description of the Related Art

Cataract surgery is one of the most successfully and most frequently performed surgical procedures in the US. Each year, millions of people achieve a dramatic improvement in their visual function thanks to this procedure. With the increasing proportion of the US population reaching their retirement years, there is expected to be a doubling of the demand for cataract surgery over the next twenty years from 3.3 million to over 6 million annually. This increased demand will require more ophthalmologists to be trained to perform cataract surgery as well as each trained ophthalmologist to perform more cataract surgeries each year.

In addition to the increase in demand for cataract surgery, there have been many technological advances that have increased patient expectations and requirements for the surgery. The procedure takes a short amount of time to perform, and patients expect quick recovery of visual function. Patients are also asking their ophthalmologist to give them restoration of more youthful vision without glasses through the use of multifocal lenses, presbyopia correcting lenses, toric lenses, and monovision to name a few. The use of these lenses requires perfect technique, perfect preoperative measurements, and a dose of good fortune to ensure patient satisfaction. In fact, as many as 20-50% of patients will typically require glasses or follow up refractive surgical enhancements to achieve their desired refractive endpoint. The reason for this high amount of refractive unpredictability comes from the final resting position of the lens implant within the eye. This is mathematically expressed as the effective lens position ("ELP"), and can be quite variable and unpredictable in the current state of cataract surgery. Recently, hundreds of millions of dollars have been invested into developing highly sophisticated femtosecond laser systems that will be able to more precisely create the cataract incisions with the stated goal of lessoning the variability of the ELP and thus aiding in better refractive outcomes. However, as good as the laser is, it does not account for the major problem plaguing the variability of the ELP, which is the volumetric difference between the cataract, natural capsular bag and intraocular lens implant, or IOL.

SUMMARY

The present invention relates to a prosthetic capsular bag and method for inserting the same. The prosthetic capsular bag addresses the above mentioned problem by helping to maintain the volume of the natural capsular bag, thereby stabilizing the effective lens position of the IOL and improving refractive outcomes with cataract surgery. The prosthetic capsular bag further provides an integrated refractive surface, providing a means for experimentally determining an effective lens position prior to inserting an IOL. Herein, the prosthetic capsular bag of the present invention is referred to as a Perfect Prosthetic Lenticular Capsule or "PPL-C."

In one embodiment, the present invention is a prosthetic capsular bag for insertion into an eye, the prosthetic capsular bag comprising an anterior surface including an opening, and a posterior surface, wherein at least a portion of the posterior surface is a refractive surface. In this embodiment, the prosthetic capsular bag is adapted to contain an intraocular lens.

In a further embodiment, the present invention is a prosthetic capsular bag for insertion into an eye, the prosthetic capsular bag having a generally discoid shape including a posterior surface, an anterior surface including an opening, and a flange extending radially from the opening.

In another embodiment, the present invention is a prosthetic barrier for separating an anterior segment and poster segment in an eye, the barrier having a generally discoid shape including a posterior surface, an anterior surface including an opening, and an exterior contour flange extending radially from the opening.

In a further embodiment, the present invention is a method for inserting and positioning an intraocular lens into a patient's eye comprising: (a) inserting a prosthetic capsular bag into the patient's eye, the prosthetic capsular bag including an anterior surface, the anterior surface having an opening, and a posterior surface, wherein at least a portion of the posterior surface is a refractive surface; (b) determining the position of the refractive surface; (c) selecting an intraocular lens based on the determined position of the refractive surface; and (d) inserting the intraocular lens into the prosthetic capsular bag.

BRIEF DESCRIPTION OF THE DRAWINGS

A better understanding of the present invention will be had upon reference to the following description in conjunction with the accompanying drawings, wherein.

DETAILED DESCRIPTION

Figure 1:
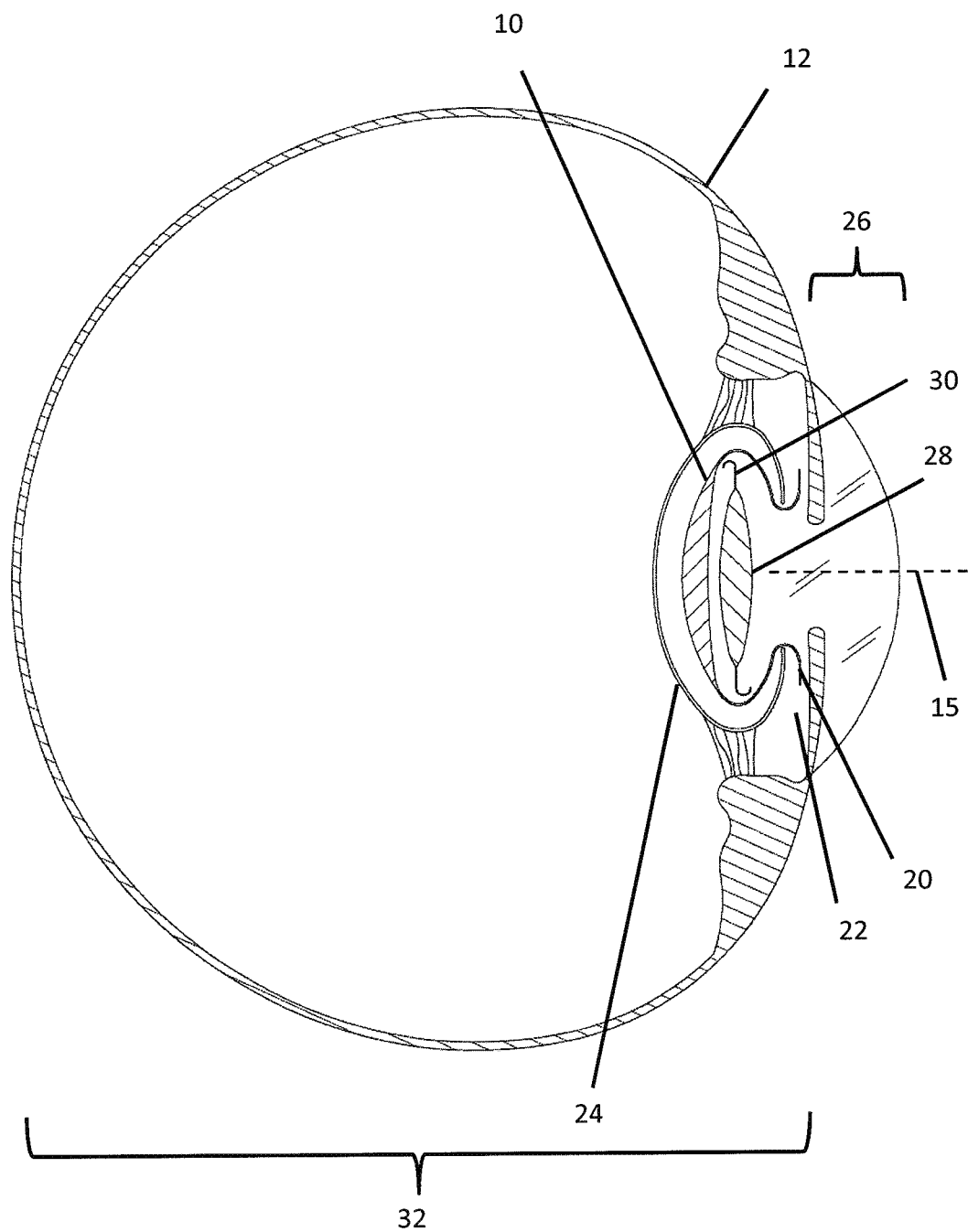
FIG. 1 depicts a cross-sectional side view of an eye including a first embodiment of a PPL-C containing an IOL.
Figure 2:
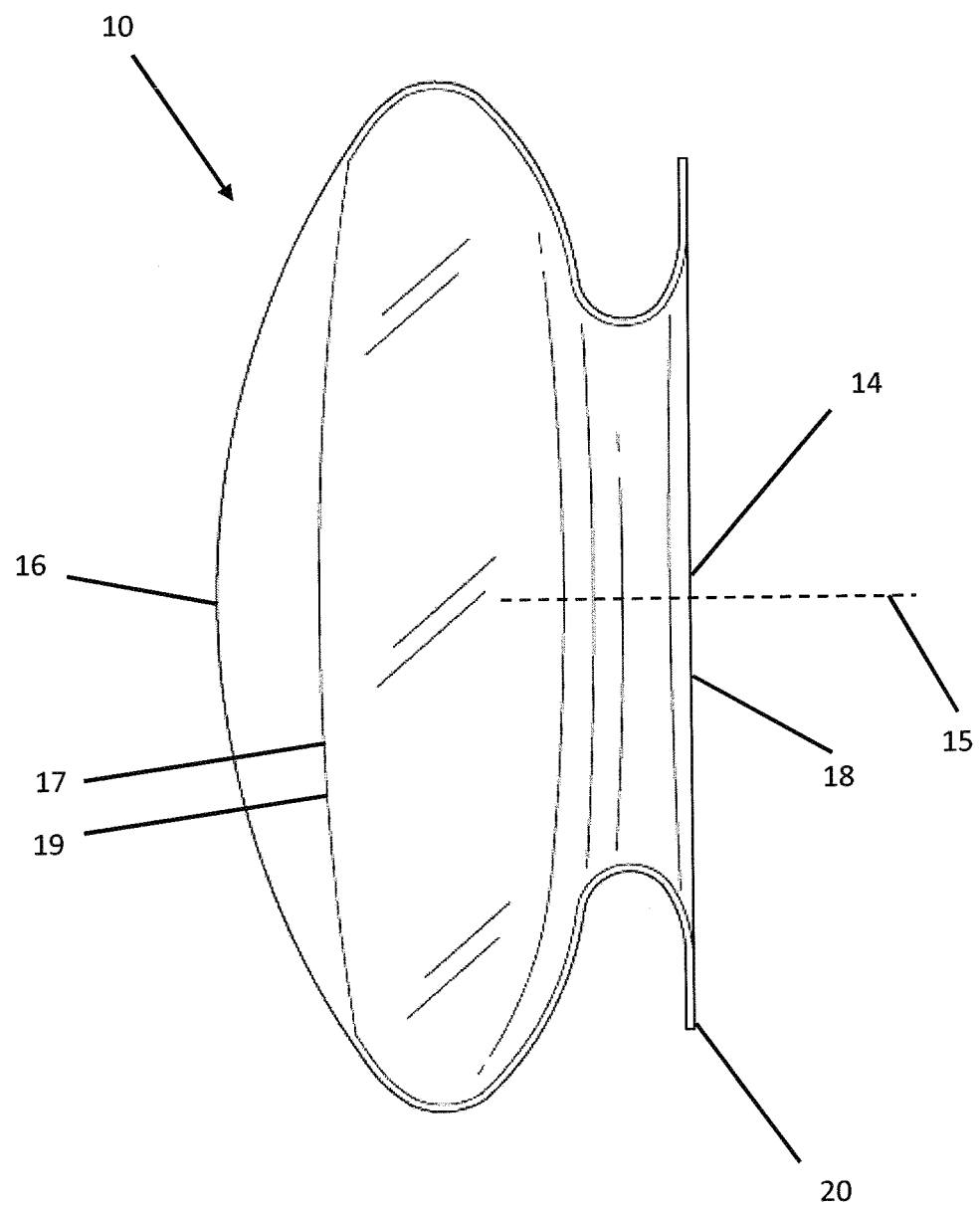
FIG. 2 depicts a side elevation view of the first embodiment of the PPL-C.
Figure 3:
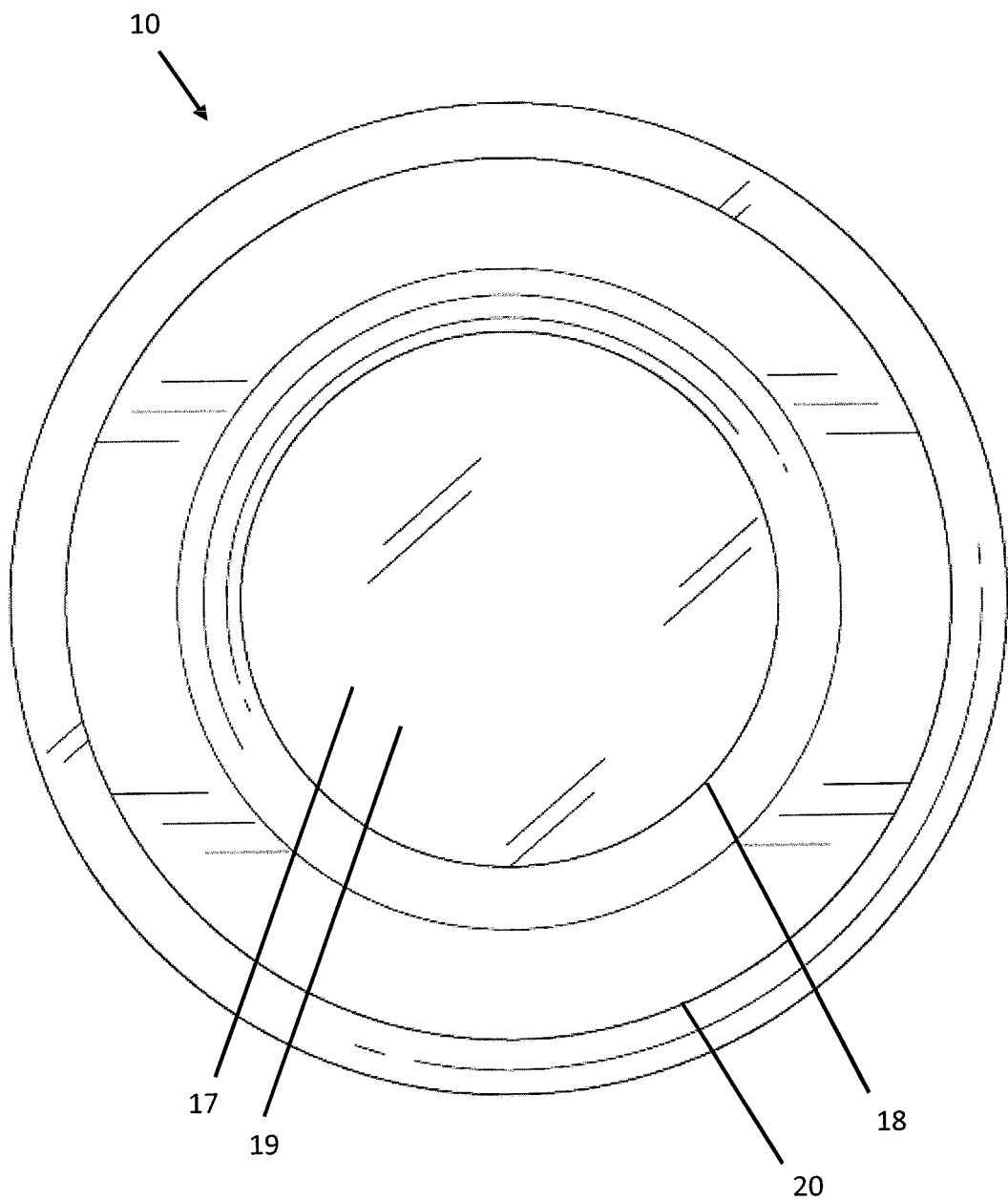
FIG. 3 depicts an anterior plan view of the first embodiment of the PPL-C.

With reference to FIGS. 1-3, the PPL-C 10 of the instant invention is shown approximating the size and shape and volume of a natural human lens. Its dimensions would be variable, so that physicians may order an implant that most closely matches the lens of the eye 12 being operated on. The human lens varies in thickness from approximately 3.5 mm to 5.5 mm. A natural lens tends to be thicker in more hyperopic eyes and thinner in more myopic eyes. Also, the lens thickens over time and increased age is associated with a thicker lens on average. The diameter of the human lens is approximately 9 mm. Therefore, in one embodiment, the PPL-C 10 would be a substantially discoid shape of approximately 4.5 mm in thickness by 9 mm in diameter. For purposes of clarity, the thickness of the PPL-C 10 is the distance between the anterior surface 14 and posterior surface 16 of the PPL-C 10 along the visual axis 15. The anterior surface 14 contains a circular opening 18 approximately 6 mm in diameter, with an exterior contour, such as, for example, a 1 mm flange 20, surrounding and extending radially from the opening 18. The flange 20 would further assist in stabilization and centration of the PPL-C 10 by extending into and fitting within the ciliary sulcus 22. This size of PPL-C 10 would function to fit precisely within the capsulorhexis created by a femtosecond laser.

At least a portion of the inner face 17 of the posterior surface 16 of the PPL-C 10 would be made of a refractive surface so that a pseudophakic refraction could be performed intraoperatively with a known lens already inside the eye, e.g. the posterior refractive surface 19. In a preferred embodiment, as shown in FIGS. 1-3, substantially the entire inner face 17 would be made of a low power refractive surface (for example +1D). While the posterior refractive surface 19 is generally discussed in terms of a +1D surface, it may be made of any and all lens powers and designs that are currently known in the art of intraocular lenses. This includes, but is not limited to: spherical, aspheric, wavefront, convex, concave, multifocal (diffractive, refractive, zonal), toric, accommodative, UV filtering, and diffractive chromatic aberration reducing lenses, and optical powers ranging from +30 to −30 diopters.

The PPL-C 10 is adapted to be implanted within the eye and is preferably made of a biologically-compatible material that would be inert inside the eye. It is preferably deformable so as to be folded and inserted via an injection system through a corneal incision ranging between about 0.1 mm and 10 mm, preferably between about 1.5 mm and 3 mm. The size of the corneal incision varies based on several factors, including the volume of the PPL-C 10, its plasticity, and the volume of the injection cartridge through which the PPL-C 10 will be delivered. The capsulorhexis must be about equal to or less than the dilated diameter of the patient's iris as the opacity of the iris forms a natural barrier for the capsulorhexis created by a femtosecond laser. A capsulorhexis created manually is typically of the same size, as direct visualization of the rhexis boundary is advisable throughout the creation process. The capsulorhexis ranges between about 3 mm and 8 mm, preferably between about 4 mm and 7 mm. During implantation, the folded PPL-C 10 passes through the corneal incision, through the capsulorhexis, and into the patient's natural capsular bag 24. The PPL-C 10 preferably also possesses sufficient elasticity to resume its pre-folded shape once positioned inside the eye.

Current intraocular lenses are made of various materials including silicone, collamer, and acrylic that have these capabilities. In preferred embodiments, the material used for the PPL-C 10 is a biologically-compatible, optically clear material similar or identical to those used in foldable intraocular lenses.

The PPL-C 10 would preferably be inserted into the patient's eye 12 through the use of an injection system. The injection system would allow the PPL-C 10 to be automatically folded into a smaller shape as it was advanced so as to allow it to fit through an incision much smaller than the diameter of the unfolded PPL-C 10. The inventor believes that injection systems already developed through which IOLs are injected into the eye, which comprise a cylindrical cartridge and an advancement rod on a screw type advancement system or plunger advancement system, would be suitable for use with the PPL-C 10.

The PPL-C 10 is preferably inserted into a patient's eye 12 with the use of a laser. A femtosecond laser would be used to create the capsulorhexis, likely after the same device was used to make the other incisions including the main wound, the paracentesis and any corneal or limbal relaxing incisions as necessary. The cataract, i.e., the patient's natural lens, would then be removed using techniques known in the art. The residual cortex would be removed using technique known in the art, such as via inspiration/aspiration. An aphakic refraction would be completed using an intraocular refracting device such as, for example, the Wavetec ORA system. An IOL calculation would be performed using an algorithm such as, for example, the Mackool algorithm. Then, the patient's natural capsular bag 24 and anterior segment 26 would be filled with viscoelastic material, and the PPL-C 10 would be loaded into the injection device. It would be folded into a small tubular shape and injected into the natural capsular bag 24. The viscoelastic material would be removed from behind the PPL-C, and from the anterior segment 26. A psuedophakic refraction would be done with a system similar to a standard auto-refractor, or the intraoperative Wavetec ORA system. This calculation would need to be done using approved protocols.

An example refraction using an approved protocol, and accompanying background information, is discussed herein. Current state of the art requires multiple independent variables to be measured so that the dependent variable of effective lens position can be estimated. These independent variables in the Holladay 2 formula (one of the most popular modern formulas) are in decreasing order of importance include: axial length, average keratometric power, horizontal white to white, refraction, anterior segment depth, lens thickness, and age. These variables are then used to estimate the ELP. However, this is simply an estimation or prediction. If this prediction is incorrect, the post-operative refractive outcome will be compromised. Therefore, emphasis should be placed on the ability to determine the ELP rather than estimating it. The PPL-C 10 will help determine the ELP in two different ways, as described in the procedure below.

Figure 4:
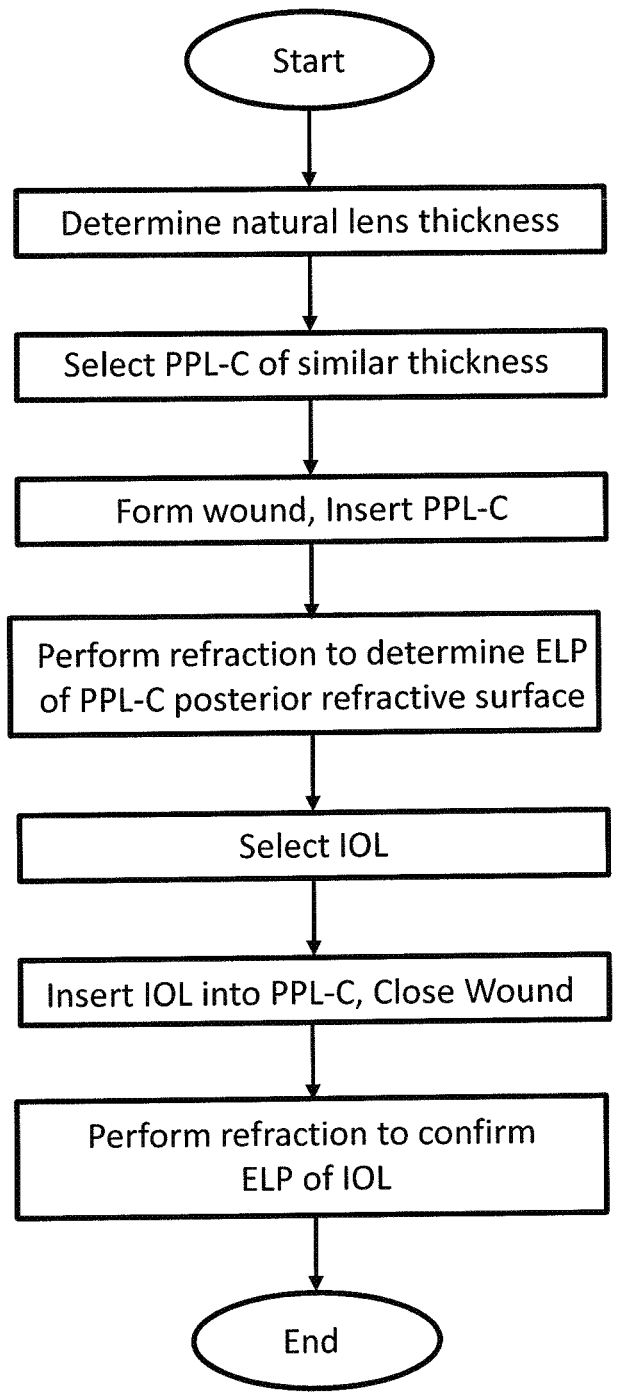
FIG. 4 is a flowchart of a method for inserting and positioning an intraocular lens into a patient's eye.

FIG. 4 is a flowchart depicting a method for inserting and positioning an intraocular lens into a patient's eye. First, the lens thickness of a patient's natural lens is determined pre-operatively using known techniques. Next, a PPL-C 10 of similar thickness will be chosen for implantation. The goal will be to select a PPL-C 10 sized such that the inner face 17 of the PPL-C 10 at the same location as the posterior surface of the patient's natural lens. When an IOL 28 is inserted within the PPL-C adjacent to the inner face 17 and centered within the PPL-C 10, that IOL 28 will be positioned in substantially the identical location previously occupied by the patient's natural lens.

A femtosecond laser is used to create the main wound, the paracentesis and any corneal or limbal relaxing incisions as necessary, and the capsulorhexis. The patient's natural lens is then removed using techniques known in the art. The residual cortex is removed using techniques known in the art, such as via inspiration/aspiration. Then, the patient's natural capsular bag 24 and anterior segment 26 are filled with viscoelastic material, and the PPL-C 10 inserted into the natural capsular bag 24. The viscoelastic material is then removed from behind the PPL-C, and from the anterior segment 26 in preparation for performing a psuedophakic refraction.

By being able to identify and control the position of the IOL 28, choosing an IOL 28 is no longer dependent upon the 7 variables for ELP. Rather, via theoretical vergence formulas, the exact IOL 28 needed to provide a desired refractive outcome can be specifically calculated with keratometric power, effective lens position and axial length. The current weakness of the formulas in place is due to the inability to accurately predict ELP. To confirm the pre-operative theoretical calculation is correct, a refraction is performed in the operating room once the PPL-C 10 is implanted in the patient's eye via a Wavetec ORA system, retinoscopy or by other known methods. The refraction will technically be a pseudophakic refraction as the posterior refractive surface 19 of the PPL-C 10 will have a refractive power, such as, for example, +1 diopter.

A method of determining the correct intraocular power for a piggyback lens is calculated by first determining the power of the IOL 28 to be implanted using the following equation:

$$IOLe = \frac{1336}{\frac{1336}{\frac{1000}{\frac{1000}{PreRx} - V} + Ko} - ELPo} - \frac{1336}{\frac{1336}{\frac{1000}{\frac{1000}{DPostRx} - V} + Ko} - ELPo}$$

ELP o=effective lens position.
K o=net corneal power.
IOL e=IOL power.
V=vertex distance.
PreRx=pre-op refraction. (Also can represent the intra-operative refraction after PPL-C has been placed)
DPostRx=desired post-op refraction.
The Effective Lens Position (ELPo) is the distance from the secondary principal plane of the cornea to the principal plane of the thin-IOL equivalent. The keratometric power of the cornea (Kk) is converted to the net optical power of the cornea (Ko) as follows: Ko=Kk*0.98765431. For example, if the Kk is 44.50 D, Ko=44.50 D*0.98765431=43.95 D. The net optical power of the cornea (Ko) would then be 43.95 D.

By comparing pre-operative theoretical IOL calculations with the aphakic refraction, the PPL-C refraction, and the post-IOL implantation refraction, surgeons can greatly improve the accuracy of their post-operative refractive outcomes.

Once the appropriate IOL 28 is selected, the PPL-C 10 and anterior segment 26 are refilled with viscoelastic material and, based on the residual refractive error, the appropriate IOL 28 is selected and inserted into the PPL-C 10. The viscoelastic material is then removed from the eye, and the wounds closed through standard methods of hydration or suturing. A final confirmatory refraction would be completed, taking great effort to ensure normal intraocular pressure, as this can affect the position of the PPL-C 10 and IOL 28 inside the eye. If there were found to be a significant error at this point, the surgeon would still have the luxury of removing the implanted IOL and replacing it with one of a more desirable refractive power, without risking damage to the fragile natural capsular bag 24, due to the protective nature of having the IOL 28 contained within the PPL-C 10.

The PPL-C 10 provides an enhanced ability to achieve desired refractive targets, with a side benefit of increased safety. This implant will provide these advantages in several ways.

First, the PPL-C 10 provides centration of the IOL 28 along the visual axis 15. A femtosecond cataract laser system has the ability to center the capsulorhexis around the visual axis 15 of the patient rather than the optical center of the cataract. The capsulorhexis is ultimately what will center the PPL-C 10 as this is the opening through which the PPL-C 10 will be inserted. The capsulorhexis is essentially juxtaposed at the center of the PPL-C 10, centering the PPL-C 10 and being stabilized via the flange 20 extending into and fitting within the ciliary sulcus 22. The flange 20 mechanically retains the PPL-C 10 centered on the patient's visual axis 15 and prevents future movement or migration of the PPL-C 10.

Centration of the IOL 28 on the visual axis 15 is extremely important to the visual function of the IOL 28 and the benefit the patient receives. Aspheric lenses have made decentration more tolerable, however centration is absolutely vital to the best visual performance of multifocal intraocular lenses. Decentration of less than 1 mm can cause significant morbidity, so much so that surgical intervention including laser pupiloplasty, IOL repositioning and IOL exchange are often needed. The PPL-C 10 is centered along the visual axis 15 via the capsulorhexis. An IOL 28 commonly includes haptics 30 which can engage opposed interior surfaces within the PPL-C 10 to maintain the centered position of the IOL 28. The outer diameter of the IOL 28, when unfolded and including the haptics 30, is substantially equal to the inner diameter of the PPL-C 10. Therefore, the IOL 28 will be in physical contact with the peripheral internal surface of the PPL-C 10, which maintains the centered position of the IOL 28 within the PPL-C 10 and also within the visual axis 15.

Second, the PPL-C 10 provides a prosthetic barrier between the anterior segment 26 and posterior segment 32 of the eye in the case of inadvertent rupture of the posterior surface of the natural capsular bag 24, or after planned YAG laser posterior capsulotomy. Despite the overall success of cataract surgery, there is still about a 2% surgical complication rate utilizing modern techniques, although this varies among individual surgeons. Residents in ophthalmology training programs have historically had complication rates around 4-7%. Most complications from cataract surgery are caused by inadvertent rupture of the natural capsular bag 24 which houses the cataract. The natural capsular bag 24 also provides an important anatomical barrier within the eye. It divides the anterior segment 26 from the posterior segment 32. The posterior segment 32 contains the vitreous body, retina, optic nerve and the central retinal artery and vein. A violation of the integrity of the barrier provided by the natural capsular bag 24 allows fluid communication between the anterior and posterior segments 26, 32, and potentially the ocular surface. Vitreous may then flow out of the posterior segment 32 according to pressure gradients, flowing from high pressure toward low pressure. This typically causes vitreous to flow directly to the surgical incision site.

Vitreous can prevent wound healing if it shifts to the surgical incision site, and more significantly can provide a conduit for microbial infections to proceed directly to the posterior segment 32. In addition to the problems caused by vitreous, a break or tear in the natural capsular bag 24 can prevent the stable implantation of an IOL within the posterior segment 32. Alternatively, surgeons can place an IOL 28 in the ciliary sulcus 22 or the anterior chamber, although each of these has their own potential complications associated with them. Therefore it is of utmost importance to keep the natural capsular bag 24 intact as there are currently no methods to consistently reestablish the integrity of the natural capsular bag 24 once it has been compromised. Should the natural capsular bag 24 be compromised, the PPL-C 10 may serve as a prosthetic barrier between the anterior segment 26 and posterior segment 32.

About 30% of all implanted intraocular lenses will develop visually significant posterior capsular opacification. If this develops, a YAG laser is used to create an opening in the posterior surface of the natural capsular bag 24 to remove this opaque membrane. However, once the hole in the natural capsular bag 24 is created, the barrier between the vitreous and the anterior segment 26 has been lost. Thus, if the lens needs to be removed after a YAG laser posterior capsulotomy has been performed, it makes the chances for serious complications rise dramatically. However, if a PPL-C 10 is placed in the natural capsular bag 24 and a YAG laser posterior capsulotomy has been performed, there is still an adequate barrier for the vitreous in place. In addition, the haptics 30 which hold the IOL 28 in place inside the PPL-C 10 are not prone to scar formation, thus making future lens removal much easier and decreasing the risk for complications during IOL exchange.

Third, the PPL-C 10 limits the chronic capsular opacification that takes place in the natural capsular bag 24 and can cause refractive shifts due to ELP change, anterior capsular phimosis, and visually significant posterior capsular opacification. After cataract surgery has been performed, the natural capsular bag 24 undergoes chronic changes. These changes are largely due to the presence of lens epithelial cells that remain on the natural capsular bag 24 after surgery. These epithelial cells continue to grow and can cause problems. For example, the anterior surface of the natural capsular bag 24 can fibrose and contract over time causing a progressively smaller aperture overtop of the lens. If the entire natural capsular bag 24 becomes fibrotic, and phimosis persists, there can be zonular dehiscence and changes to the effective lens position over time. In addition, about 30% of the time, the posterior surface of the natural capsular bag 24 becomes significantly opacified requiring a YAG laser posterior capsulotomy. The effect of limiting epithelial cell migration and propagation would largely be mediated by the type of material used in forming the PPL-C 10, however hydrophobic acrylic materials tend to be most efficacious of all known and used IOL materials.

Fourth, the PPL-C 10 helps maintain the effective lens position of an IOL 28 implanted into the eye. Precisely matching the preoperative dimensions of the cataract with the PPL-C 10 enhances a physician's ability to predict the ELP of the lens implant. Currently, the ELP of an IOL 28 is estimated based on a number of factors, including the depth of the anterior segment 26, lens thickness, and white to white diameter, among others. However, these measurements are simply used to predict the ELP. The accuracy of the prediction is actually quite low, resulting in only 50% of patients being within a tolerable level of their refractive goal post-cataract surgery. While other dimensions of the eye required for IOL calculation can be measured quite precisely and accurately, the ELP has remained the elusive last great variable to conquer in the quest for highly accurate and predictable IOL calculations for cataract surgery.

The reason for the great variability in the ELP is due to the volumetric difference between the cataract and the IOL. The average thickness of the human cataract at age 65 is approximately 4.5 mm, however this varies from patient to patient. In contrast, an IOL 28 is typically less than 1 mm thick. This volumetric difference allows for pressure differentials between the posterior segment 32 and the anterior segment 26, as well as contraction of the natural capsular bag 24 to shift the final resting position of the IOL 28. The lens thickness will be measured preoperatively and a PPL-C 10 with a corresponding volume and thickness will be implanted. By implanting a PPL-C 10, the volume of the natural capsular bag 24 is effectively held constant. It resists forces that would otherwise shift it and its contents anteriorly or posteriorly. This stability of lens capsule volume will make IOL calculations much more accurate.

Fifth, the PPL-C 10 allows for an intraoperative pseudophakic refraction while still allowing another IOL to be implanted without explanting the original lens. Recently, there have been advances in IOL calculation methodologies that use intraoperative refraction devices, such as the Wavetec ORA and Orange systems, to provide better refractive outcomes. These devices can perform aphakic refractions, pseudophakic refractions, and assist with the alignment of toric IOLs and assist with Limbal Relaxing Incisions. Aphakic refractions do not have the benefit of any lens inside the eye, so ELP is still a variable that this data cannot account for. Pseudophakic refractions can be helpful, but it provides the information only after the IOL has been implanted. If the data shows a different lens would be more beneficial, it would require the physician to explants the lens and implant a different one. Explanting a lens takes time, effort and skill, and can cause damage to the cornea or other structures within the eye. Using a PPL-C 10 with a low power lens incorporated into its posterior surface, e.g., the posterior refractive surface 19, allows a physician to perform a pseudophakic refraction with this refractive surface, and still provides the physician the ability to implant a second lens, e.g., the IOL 28, within the PPL-C 10 that will make up the refractive difference as measured by the intraoperative refraction device, such as the Wavetec ORA.

Sixth, the PPL-C 10 may serve as a means for pharmaceutical delivery. Pharmaceuticals, drugs, medications, such as, for example, slow release medicine pellets, or other substances intended for introduction into the eye may be placed within PPL-C 10 outside of the visual axis 15 in a location that is not subject to sequestration by membrane formation. There is a tremendous amount of research and demand for a slow release implant that would essentially eliminate the need for post cataract surgery eye drops. The PPL-C 10 would be a suitable receptacle for such an implant as the periphery of the interior of the PPL-C provides a location outside of the visual axis 15, in constant contact with the aqueous humor, without risk of becoming encapsulated by scarring, and prevents the implant from damaging natural intraocular structures. Due to the prosthetic material of the PPL-C 10, there would be no risk of membrane formation or encapsulation. Dissolved or suspended pharmaceuticals would not affect the patient's vision and could be introduced directly into the PPL-C 10 during the implantation surgery. Larger pharmaceuticals, such as slow release medicine pellets, may be shaped to mechanically maintain their position with respect to the PPL-C 10. For example, a slow release medicine pellet may be constructed with a generally toroidal shape sized to fit within the PPL-C, while remaining in the peripheral space and not obstructing the visual axis 15.

Seventh, the PPL-C 10 provides physicians with the ability to perform a lens exchange in the future that will have much less risk of damage to the natural capsular bag 24 and zonular apparatus. As stated above, if a PPL-C 10 is placed in the natural capsular bag 24 and a YAG laser posterior capsulotomy has been performed, there is still an adequate barrier for the vitreous in place. In addition, the haptics 30 which hold the IOL 28 in place inside the PPL-C 10 are not prone to scar formation, thus making future lens removal much easier.

Figure 5:
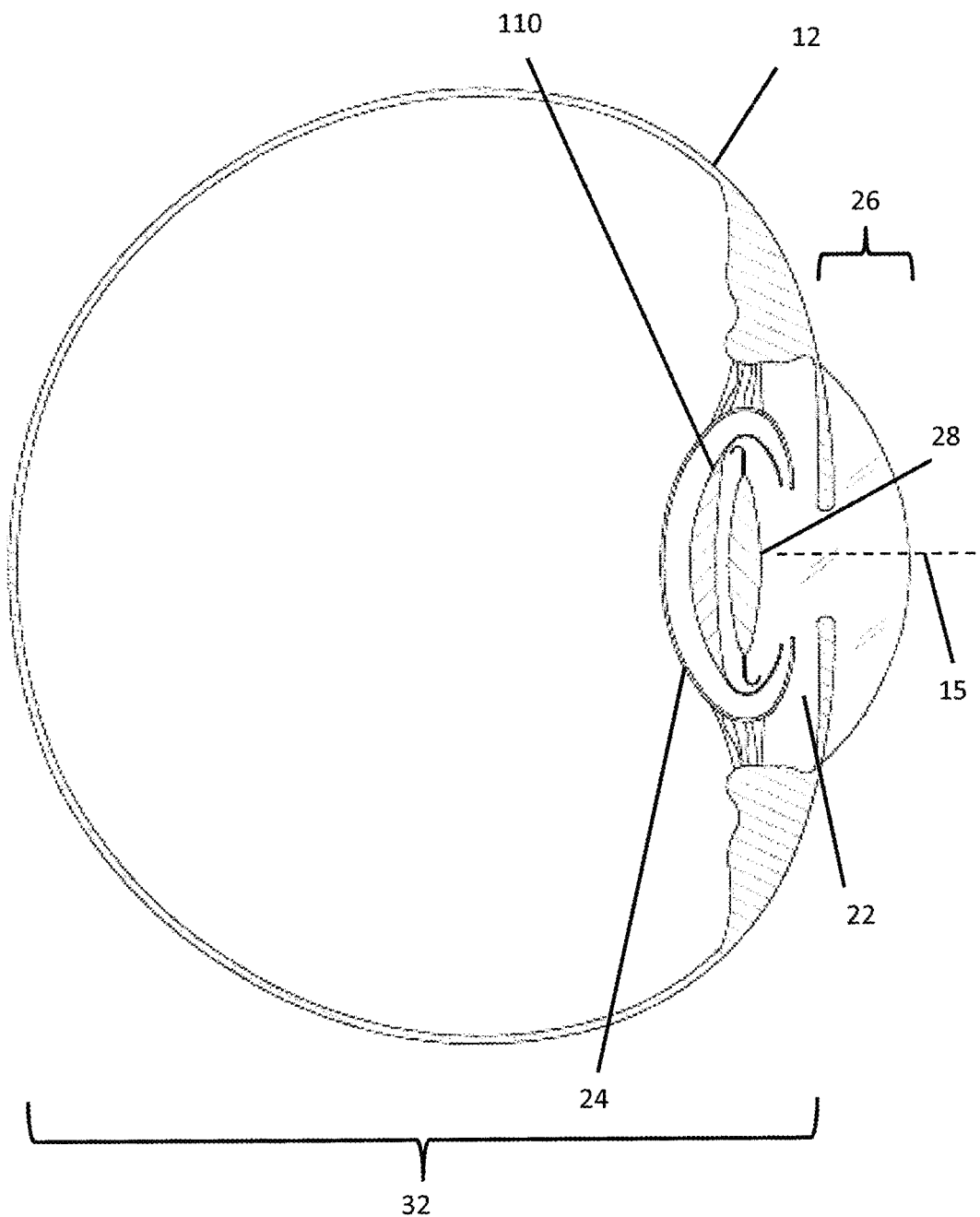
FIG. 5 depicts a cross-sectional side view of an eye including a second embodiment of a PPL-C containing an IOL.
Figure 6:
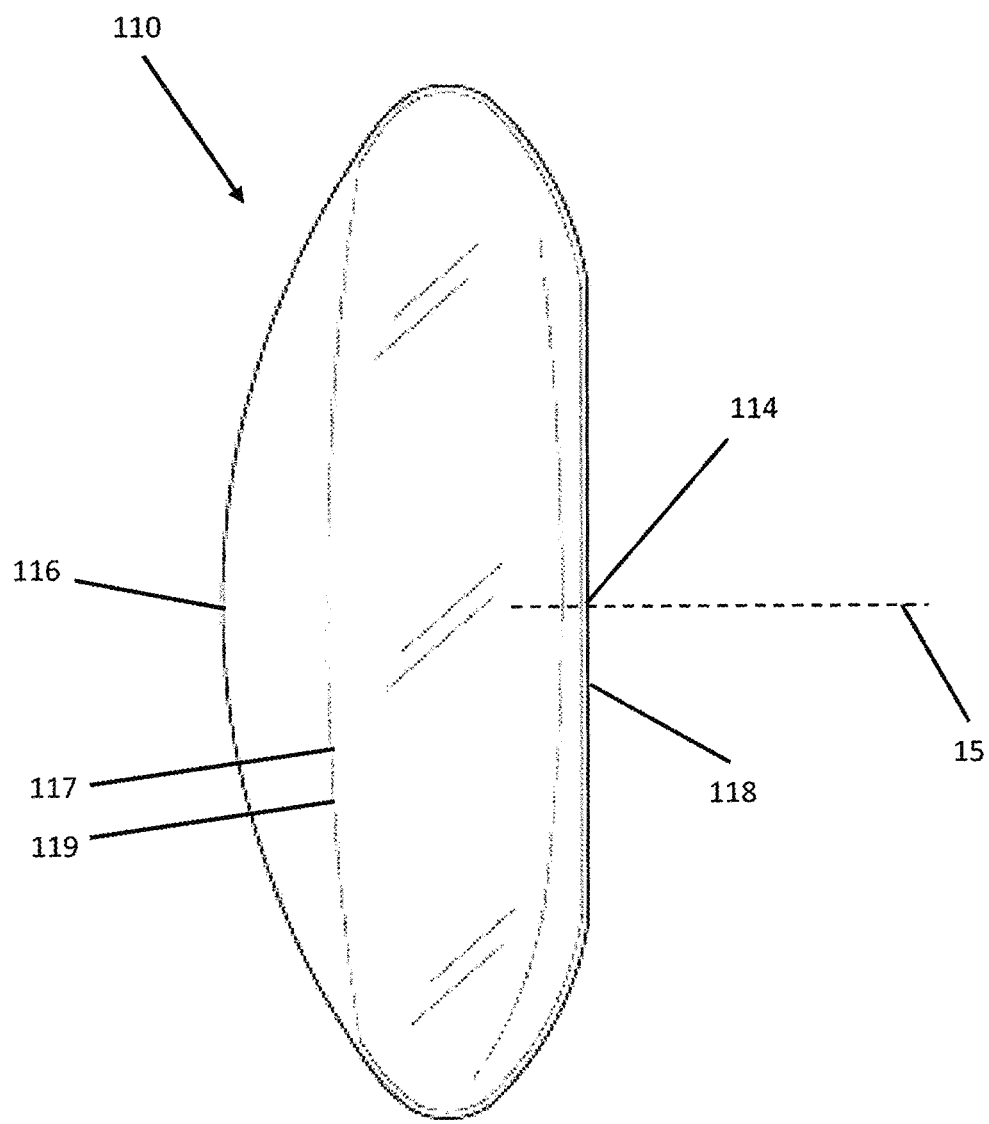
FIG. 6 depicts a side elevation view of the second embodiment of the PPL-C.
Figure 7:
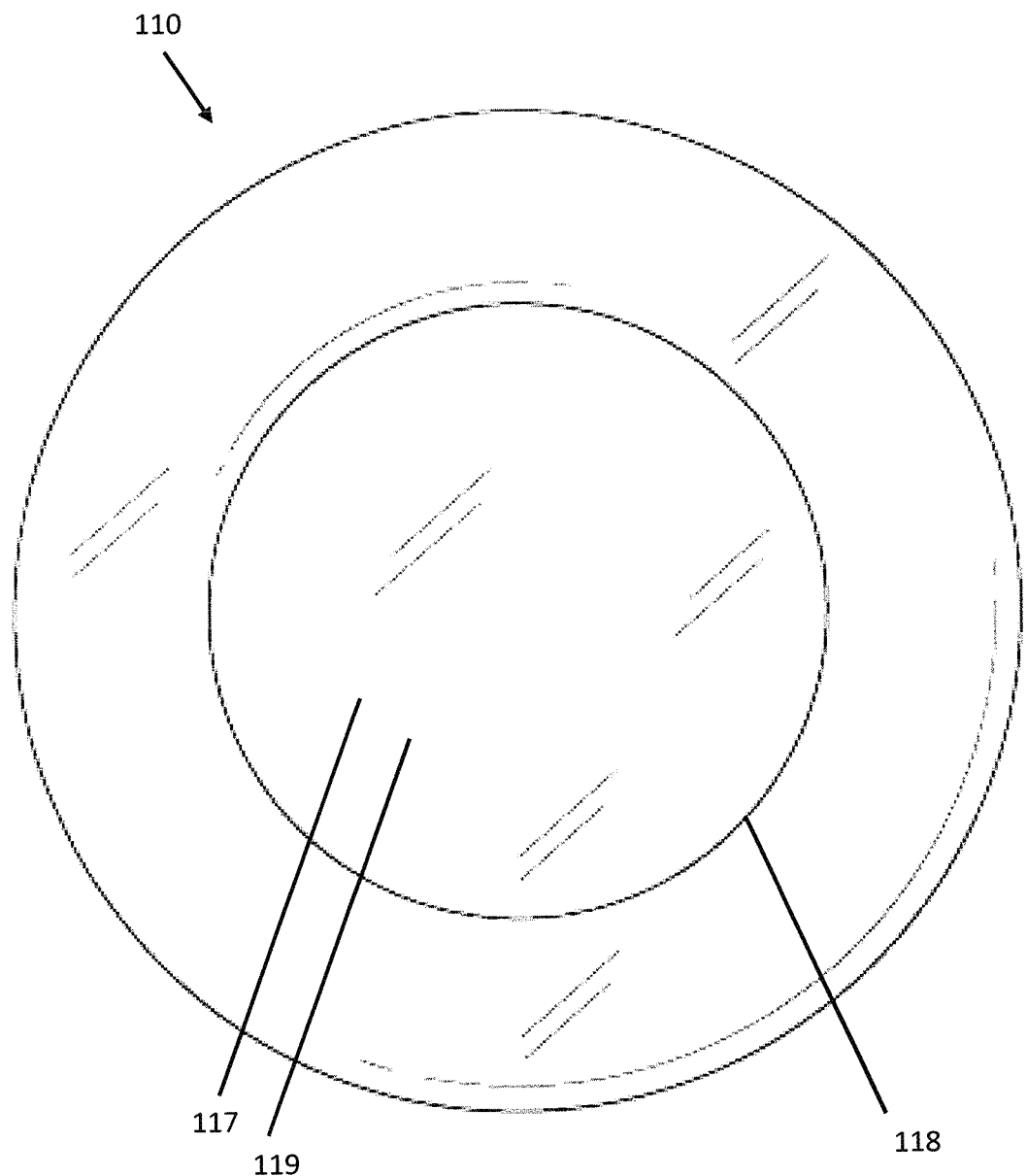
FIG. 7 depicts an anterior plan view of the second embodiment of the PPL-C.

FIGS. 5-7 depict a second embodiment of the present invention. In this embodiment, the PPL-C 110 is a substantially discoid shape of approximately 4.5 mm in thickness by 9 mm in diameter. The thickness of the PPL-C 110 is the distance between the anterior surface 114 and posterior surface 116 of the PPL-C 110 along the visual axis 15. The anterior surface 114 contains a circular opening 118 approximately 6 mm in diameter. At least a portion of the inner face 117 of the posterior surface 116 of the PPL-C 110 is made of a refractive surface, e.g. the posterior refractive surface 119. This second embodiment of differs from the first embodiment in that the PPL-C 110 lacks a flange and would therefore not be mechanically fixated or centered on the capsulorhexis. Rather, the volume of the PPL-C 110 relative to the opening of the capsulorhexis would keep the device in place much in the same way current single piece IOLs are folded and placed within the natural capsular bag.

This second embodiment PPL-C 110 sacrifices a measure of stability as compared to the first embodiment PPL-C 10. However, without a flange, this second embodiment is usable for non-femtosecond laser cataract removal, i.e. traditional manual phacoemulsification, and may be particularly useful for surgeons who lack access to a femtosecond laser.

In a third embodiment, the lenticular surface on the posterior aspect of the device would have a plano powered lens. Some extreme myopes would not benefit from a +1D refractive surface as they may be in need of a negative IOL power. For patients with these conditions, a PPL-C may be used with a plano or zero power posterior lenticular surface.

In a fourth embodiment, the PPL-C has a −1D posterior refractive lenticular surface as some extreme axial myopes (about 30 mm and beyond) may require this type of lens.

In a fifth embodiment, the posterior refractive surface 19 is a multifocal lenticular surface rather than a standard monofocal +1D surface, which would aid in presbyopia correction. This multifocal lenticular surface includes, but is not limited to, refractive, diffractive, and zonal multifocal refractive technology. Typically, a multifocal lens would be designed to provide multiple focal points that would range from plano, e.g., 0 diopters, to +3D at the spectacle plane.

In a sixth embodiment, the posterior refractive surface 19 includes a spherical and cylinderic (astigmatic) lenticular surface so as to aid in the correction of pre-existing and surgically induced corneal astigmatism. As most surgeons induce between −0.25 D and −0.50 D of astigmatism with their corneal incisions required for cataract surgery, it would be beneficial even for most patients with spherical corneas to have this neutralized. The diopteric power of the toric correction could increase up to 6 diopters for patients with even higher amounts of astigmatism.

The foregoing detailed description is given primarily for clearness of understanding and no unnecessary limitations are to be understood therefrom for modifications can be made by those skilled in the art upon reading this disclosure and may be made without departing from the spirit of the invention.

What is claimed is:

1. A method of manufacturing an ophthalmic implant device for implantation in an eye, the method comprising:
   manufacturing the ophthalmic implant device from silicone, the ophthalmic implant device configured to be inserted into a natural capsular bag of an eye after removal of a cataract, the ophthalmic implant device comprising:
   an anterior side including an opening;
   a posterior side; and
   a deformable sidewall, the deformable sidewall forming a single continuous wall from the anterior side to the posterior side;
   wherein the ophthalmic implant device is configured to mechanically maintain substantially a volume of the natural capsular bag,
   wherein the ophthalmic implant device is configured to mechanically self-expand;
   wherein the ophthalmic implant device is adapted to contain one or more intraocular lenses.

2. The method of claim 1, further comprising manufacturing the ophthalmic implant device from silicone and a secondary a biologically-compatible, optically clear material.

3. The method of claim 2, wherein the biologically-compatible, optically clear material comprises at least one of the following materials: collamer and acrylic.

4. The method of claim 1, wherein the ophthalmic implant device is foldable.

5. The method of claim 1, wherein the one or more intraocular lens is configured to be placed in physical contact with a peripheral internal surface of the deformable sidewall.

6. The method of claim 1, wherein the one or more intraocular lens comprises a refractive surface.

7. The method of claim 6, wherein the exterior contour is adapted to mechanically maintain the ophthalmic implant device at a specific position and orientation within the eye.

8. The method of claim 1, wherein the one or more intraocular lens comprises one or more haptics.

9. The method of claim 8, wherein the one or more haptics are configured to physically contact a peripheral internal surface of the deformable sidewall.

10. The method of claim 1, wherein the one or more intraocular lens includes at least one or more of the following characteristics: concave, convex, spherical, aspheric, wavefront, multifocal diffractive, multifocal refractive, multifocal zonal, accommodative, UV filtering, diffractive chromatic aberration reducing, and astigmatism correcting toric form.

11. The method of claim 1, wherein a portion of the ophthalmic implant device is adapted to lie within the natural capsular bag and is shaped such that an exterior contour of the ophthalmic implant device conforms to a shape of the natural capsular bag.

12. The method of claim 1, wherein the ophthalmic implant device is a biological compatible, deformable ophthalmic implant device.

13. The method of claim 1, wherein the ophthalmic implant device is substantially discoid in shape.

14. The method of claim 1, wherein the ophthalmic implant device is approximately the size, shape, and volume of a natural human lens.

15. The method of claim 1, wherein the opening is configured to be open when the ophthalmic implant device is inserted in the eye.

16. The method of claim 1, wherein the ophthalmic implant device comprises a prosthetic barrier separating an anterior segment and posterior segment of the eye.

17. The method of claim 1, wherein the ophthalmic implant device possesses sufficient elasticity to resume its pre-folded shape once positioned in the eye.

18. The method of claim 1, wherein the deformable sidewall is oriented between the anterior side and the posterior side.

19. The method of claim 1, the ophthalmic implant device configured to receive pharmaceuticals for delivery to the eye.

20. The method of claim 1, the ophthalmic implant device configured to enable a future lens exchange of the one or more intraocular lenses.

21. A method of manufacturing an ophthalmic implant device for implantation in an eye, the method comprising:
    manufacturing the ophthalmic implant device from acrylic, the ophthalmic implant device configured to be inserted into a natural capsular bag of an eye after removal of a cataract, the ophthalmic implant device comprising:
        an anterior side including an opening;
        a posterior side; and
        a deformable sidewall, the deformable sidewall forming a single continuous wall from the anterior side to the posterior side;
        wherein the ophthalmic implant device is configured to mechanically maintain substantially a volume of the natural capsular bag,
        wherein the ophthalmic implant device is configured to mechanically self-expand;
        wherein the ophthalmic implant device is adapted to contain one or more intraocular lenses.

22. The method of claim 21, further comprising manufacturing the ophthalmic implant device from acrylic and a secondary a biologically-compatible, optically clear material.

23. The method of claim 22, wherein the biologically-compatible, optically clear material comprises at least one of the following materials: collamer and silicone.

24. The method of claim 21, wherein the ophthalmic implant device is foldable.

25. The method of claim 21, wherein the one or more intraocular lens is configured to be placed in physical contact with a peripheral internal surface of the deformable sidewall.

26. The method of claim 21, wherein the one or more intraocular lens comprises a refractive surface.

27. The method of claim 21, wherein the one or more intraocular lens comprises one or more haptics.

28. The method of claim 27, wherein the one or more haptics are configured to physically contact a peripheral internal surface of the deformable sidewall.

29. The method of claim 21, wherein the one or more intraocular lens includes at least one or more of the following characteristics: concave, convex, spherical, aspheric, wavefront, multifocal diffractive, multifocal refractive, multifocal zonal, accommodative, UV filtering, diffractive chromatic aberration reducing, and astigmatism correcting toric form.

30. The method of claim 21, the ophthalmic implant device configured to receive pharmaceuticals for delivery to the eye.

* * * * *

UNITED STATES PATENT AND TRADEMARK OFFICE
CERTIFICATE OF CORRECTION

PATENT NO. : 11,033,381 B2
APPLICATION NO. : 17/157669
DATED : June 15, 2021
INVENTOR(S) : Gary N. Wortz It is certified that error appears in the above-identified patent and that said Letters Patent is hereby corrected as shown below:

On the Title Page

In Column 2, item (56), U.S. Patent Documents, Line 3, delete "10/1983" and insert --09/1983--.

On page 2, in Column 1, item (56), U.S. Patent Documents, Line 59, delete "Portnoy" and insert --Portney--.

On page 4, in Column 2, item (56), Other Publications, Line 23, delete "posiiton" and insert --position--.

On page 4, in Column 2, item (56), Other Publications, Line 25, delete "Opinoin" and insert --Opinion--.

In the Specification

In Column 2, Line 56, delete "IOL." and insert --IOL;--.

In Column 2, Line 65, delete "IOL." and insert --IOL;--.

In Column 4, Line 39, delete "psuedophakic" and insert --pseudophakic--.

In Column 5, Line 14 (approx.), delete "psuedophakic" and insert --pseudophakic--.

In Column 5, Line 43 (approx.), delete "ELP o" and insert --ELPo--.

In Column 5, Line 44 (approx.), delete "K o" and insert --Ko--.

In Column 5, Line 45 (approx.), delete "IOL e" and insert --IOLe--.

In Column 5, Line 48, delete "placed)" and insert --placed).--.

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*

In Column 6, Line 34, delete "pupiloplasty," and insert --pupilloplasty,--.

In Column 9, Line 57, delete "cylinderic" and insert --cylindrical--.

In Column 9, Line 63, delete "diopteric" and insert --dioptric--.